United States Patent [19]

Imai

[11] Patent Number: 4,482,767
[45] Date of Patent: Nov. 13, 1984

[54] PROCESS FOR PRODUCTION OF ALCOHOLS AND LPG

[75] Inventor: Tamotsu Imai, Mt. Prospect, Ill.

[73] Assignee: UOP Inc., Des Plaines, Ill.

[21] Appl. No.: 563,439

[22] Filed: Dec. 20, 1983

[51] Int. Cl.³ .......................................... C07C 29/04
[52] U.S. Cl. .................................. 568/899; 568/895;
568/896; 568/897; 568/898; 568/900; 568/901;
585/258; 585/264
[58] Field of Search ............................. 568/895–901;
585/258, 264

[56] References Cited

U.S. PATENT DOCUMENTS

| | | | |
|---|---|---|---|
| 3,209,052 | 9/1965 | Scott et al. | 568/899 |
| 3,277,191 | 10/1966 | Mosely | 568/899 |
| 3,450,777 | 6/1969 | Mizutani et al. | 260/641 |
| 3,452,106 | 6/1969 | Sato et al. | 260/641 |
| 3,758,615 | 9/1973 | Izumi et al. | 260/641 |
| 3,994,983 | 11/1976 | Webers et al. | 260/641 |
| 4,267,397 | 5/1981 | Schmidt et al. | 568/899 |
| 4,307,257 | 12/1981 | Sada et al. | 568/899 |
| 4,340,769 | 7/1982 | Brandes et al. | 568/899 |
| 4,393,256 | 7/1983 | Schmidt | 568/907 |

OTHER PUBLICATIONS

Hydrocarbon Processing, Nov. 1981, p. 173, "Isopropanol".

Primary Examiner—J. E. Evans
Attorney, Agent, or Firm—William H. Page, II; John F. Spears, Jr.

[57] ABSTRACT

A hydrocarbon conversion process is disclosed for the production of lower alcohols and LPG from a mixture of C₃-minus paraffins and olefins. The feed stream is passed into a hydration zone wherein portions of the ethylene and propylene are converted to ethanol and propanol. The hydrocarbons which are not hydrated are passed into a hydrogenation zone wherein the remaining olefins are converted to paraffins. The feed stream is preferably a hydrogen-containing C₁ to C₃ cut separated from the effluent of a fluidized catalytic cracking unit.

13 Claims, 1 Drawing Figure

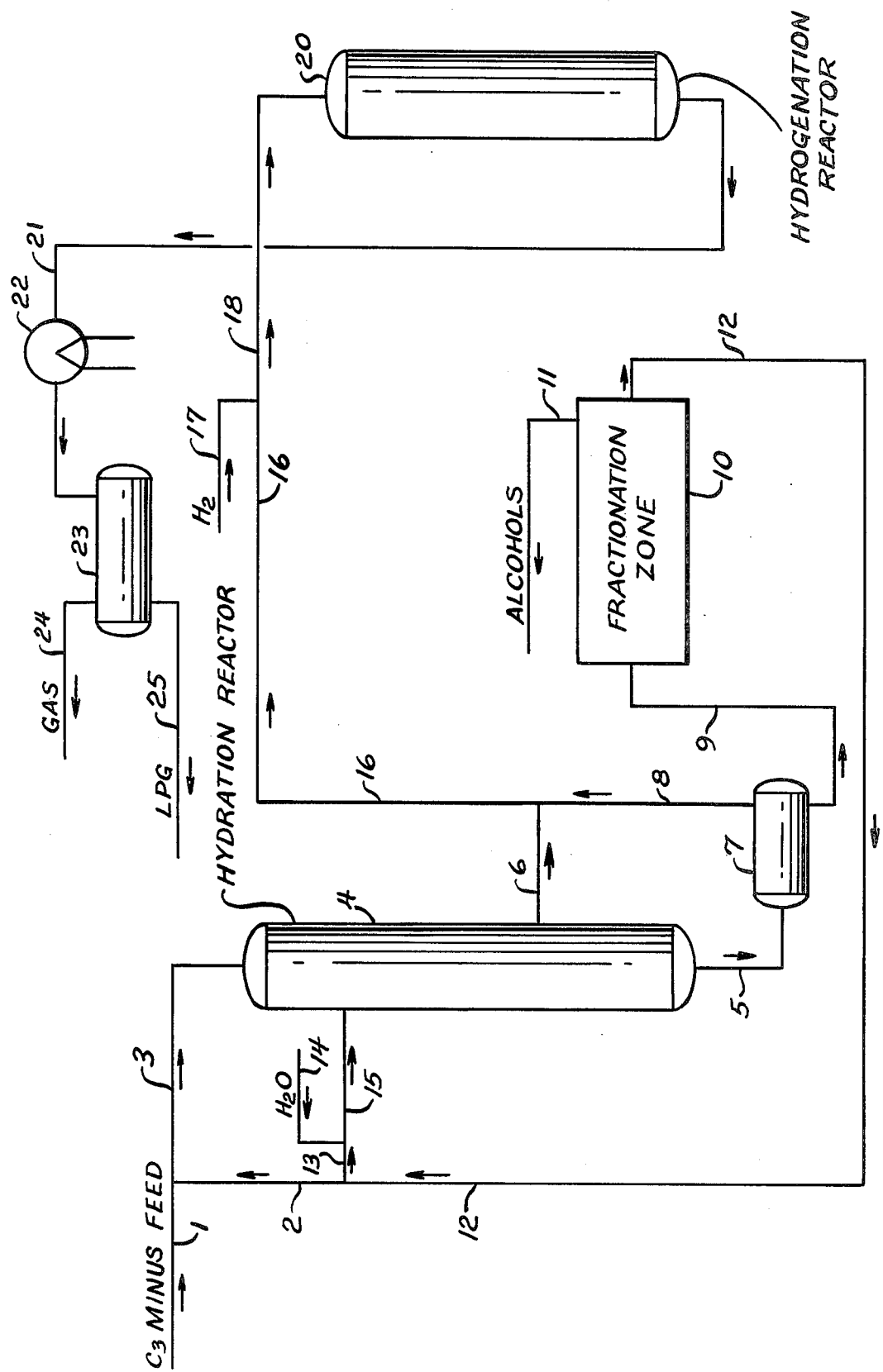

PROCESS FOR PRODUCTION OF ALCOHOLS AND LPG

FIELD OF THE INVENTION

The invention relates to a process in which light olefins are converted to the corresponding monohydric alcohols by direct hydration. The subject process is directly concerned with the production of ethanol and propanol from ethylene and propylene present in a mixture of $C_1$ to $C_3$ hydrocarbons. The invention specifically relates to a process for producing both ethanol and propanol and LPG from the $C_3$-minus light gases produced in a fluidized catalytic conversion zone. This process includes separate catalytic reaction zones for olefin hydration and olefine hydrogenation.

INFORMATION DISCLOSURE

The production of alcohols by the hydration of olefins is one of the oldest commercial petrochemical processes. Among the eariliest processes for the production of isopropyl alcohol were the so-called indirect hydration processes. A basic form of this type of process comprises the reaction of the olefin with sulfuric acid of various concentrations to produce alkylsulfates which are then hydrolyzed to produce the corresponding alcohols. A modern version of this indirect hydration is described in U.S. Pat. No. 4,393,256 (R. J. Schmidt). This reference is pertinent for its teaching that the olefins in the feed gas stream may comprise a mixture of gases containing from 2 to about 4 carbon atoms per molecule. It also describes the general utility of hydration processes for alcohol production.

Processes for the direct hydration of olefins have been developed because of various problems of indirect hydration such as high energy consumption, pollution control difficulties and the use of corrosive mineral acids. In a preferred direct hydration process, an ion exchange-type resin catalyst is employed. The overall flow of such a process is shown at page 173 of the November 1981 issue of *Hydrocarbon Processing*. Further details on the preferred reactor system and resin-type catalyst are available from U.s. Pat. Nos. 3,994,983 (W. Webers et al) and 4,340,769 (Günter Brandes et al).

Tungsten-containing catalyst systems for direct hydration of light olefins are disclosed in U.S. Pat. Nos. 3,450,777 (Y. Mizutani et al), 3,758,615 (Y. Izumi et al), and 3,452,106 (F. Sato et al). These catalysts have the advantage of being more tolerant to the higher temperatures required for ethylene hydration than resin-type catalysts.

U.S. Pat. No. 4,267,397 issued to R. J. Schmidt and the applicant describes yet another catalyst system for the direct hydration of $C_2$ to $C_4$ olefins.

The hydrogenation of light olefins is a very mild hydrotreating process step. Those skilled in the art may perform such a procedure using established methods and commercially available catalyst.

BRIEF SUMMARY OF THE INVENTION

The invention provides a process for converting a mixture of light olefins and paraffins into product streams of lower alcohols and LPG. The subject process allows the production of these different products without the use of extensive and costly separation steps to provide high purity process streams. It is thus highly useful in such installations as petroleum refineries in which it is desired to utilize olefins in a $C_3$-minus off-gas stream without extensive processing.

A broad embodiment of the invention may be characterized as a process for the production of lower alcohols which comprises the steps of passing a feed gas stream which comprises hydrogen, methane, ethane, ethylene, propane, and propylene into a hydration zone operated at conditions effective to convert a portion of the entering olefins to alcohols and thereby producing a hydration zone effluent stream which comprises hydrogen, methane, ethane, ethylene, propane, propylene, ethanol, and propanol; separating an alcohol product stream comprising ethanol and propanol from the hydration zone effluent stream and thereby forming a process stream which comprises hydrogen, methane, ethane, ethylene, propane, and propylene; passing the process stream, with additional hydrogen if needed, through a hydrogenation zone operated at conditions effective to saturate ethylene and propylene and producing a hydrogenation zone effluent stream; and, recovering an LPG product stream comprising propane from the hydrogenation zone effluent stream.

DESCRIPTION OF DRAWING

A $C_3$-minus feed stream comprising various light hydrocarbons including hydrogen, ethylene and propylene produced in a fluidized catalytic cracking process is fed to the subject process in line 1. A recycle stream comprising water carried by line 2 is admixed into the feed stream and the resultant admixture is passed into the hydration reactor 4 through line 3. In the reactor, the admixture of hydrocarbons and water is passed downward through beds of a hydration catalyst. Recycle water from line 13 together with makeup water from line 14 are passed into an upper portion of the reactor through line 15 to cool the reactants. A vapor phase stream comprising methane is removed from a lower portion of the reactor through line 6. The majority of the materials which enter the reactor are removed as a liquid phase stream withdrawn through line 5 and passed into a separation vessel 7. The liquids flowing through line 5 are preferably flashed to a lower pressure prior to passage into the vessel 7 thereby releasing the majority of the hydrocarbons as a vapor phase stream removed through line 8. The remaining liquids comprising water having dissolved therein the product ethanol and propanol are removed through line 9 and passed into a fractionation zone 10. The product alcohols may be withdrawn through one or more lines represented by line 10 as separate products or as a mixture, with this being determined by the complexity of the fractionation. The remaining water is concentrated into a stream removed through line 12 for recycling to the hydration reactor.

The vapor removed from the reactor 4 through line 6 for the purpose of pressure control together with the hydrocarbon-rich vapors removed from the separation vessel through line 8 are passed into line 16 and admixed with additional hydrogen from line 17 if necessary. This admixture is passed through line 18 into a hydrogenation reactor 20. In this reactor, the entering hydrocarbons which comprise an admixture of hydrogen, methane, ethane, propane, ethylene, and propylene are contacted with a solid hydrogenation catalyst maintained at hydrogenation conditions. This affects the saturation of the entering olefins. A hydrogenation zone effluent stream is removed in line 21 and passed through a cooler 22. This effluent stream, which is substantially free of olefinic hydrocarbons, is at least partially condensed in the cooler 22. The resulting mixed phase hydrocarbon stream flows into the separation vessel 23 in which it is divided into an off-gas stream removed through line 24 and a stream of LPG removed through line 25. This schematic diagram of the subject process has been simplified by the deletion of a large amount of apparatus normally associated with a process of this nature including fractionation column overhead and reboiler systems, flow, temperature, and pressure control systems, vessel internals, etc. This presentation of one embodiment of the invention is not intended to preclude from the scope of the subject invention those other embodiments set out herein or which result from the normal and expected modification of those embodiments.

DETAILED DESCRIPTION

Low molecular weight aliphatic alcohols are valuable and widely used industrial chemicals. For instance, isopropyl alcohol may be used as a solvent in coatings and inks, as an anti-bacterial agent, and in cosmetics. The subject process may be employed in the production of relatively high purity alcohol streams as would be used in these applications. However, the invention is primarily directed to the production of fuel-grade alcohols. For instance, isopropyl alcohol is a desirable gasoline blending component due to its high octane number. Fuel-grade isopropyl alchol may contain significant amounts of by-products, up to 5 or possibly 10 wt.%, such as ethers and ketones. Alcohols may also normally be employed as gasoline blending components when they contain a small amount of water. Water concentrations on the order of 0.5 wt.% are normally tolerable.

Most sizable petroleum refineries employ a hydrocarbon conversion unit referred to as a fluidized catalytic cracking unit. In this unit, a charge stream of a material such as a gas oil is converted to higher value more volatile hydrocarbon mixtures including naphtha. Fluidized catalytic cracking units, commonly referred to as FCC units, also generate a sizable amount of light gases. This gas has a sizable concentration of olefins such as ethylene, propylene, and butylenes. The off-gas of an FCC unit has become a standard source of light olefins consumed in petroleum refining processes such as alkylation processes which produce large amounts of high octane motor fuel. The vaporous effluent of the fractionation column associated with the FCC unit is normally processed in a unit referred to as a gas concentration unit to recover the available gasoline boiling range hydrocarbons and valuable light hydrocarbons such as $C_3$ and $C_4$ hydrocarbons. The remaining hydrogen and $C_2$ and $C_1$ hydrocarbons are often discharged from this unit as an off-gas stream, which may contain a small amount of $C_3$ and $C_4$ hydrocarbons including olefins. There is seldom any attempt to recover the hydrogen or ethylene from this off-gas stream and it is normally employed as a fuel within the refinery. Depending on the design and operation of the gas concentration unit, the off-gas stream may also contain significant amounts of propane and propylene. Further description of FCC gas concentration units is available from standard references such as U.S. Pat. Nos. 2,939,834 and 3,122,496 and the text *Petroleum Refinery Engineering*, 4th Edition by W. L. Nelson.

It is an objective of the subject invention to provide a process for upgrading a $C_3$-minus product stream of a fluidized catalytic cracking unit or an off-gas stream of a gas concentration unit of a fluidized catalytic cracking unit. It is a specific objective of the subject invention to provide a method to increase the value of the $C_3$-minus product stream or the off-gas stream of an FCC gas concentration unit. That is, it is desired to consume the hydrogen and ethylene present in these gases in a conversion process rather than simply burning them as fuel. A further objective of the subject invention is to provide a process for the production of fuelgrade alcohols which may be employed in a petroleum refinery. Another objective is to increase the quentity or quality of LPG recovered from an FCC unit.

The feed stream to the subject process comprises an admixture of two or more light olefins. Preferably, the feed stream comprises an admixture of ethylene and propylene. Admixtures such as these are available from several different sources. The preferred source of the feed material is the $C_3$-minus products of an FCC process or the off-gas stream of an FCC gas concentration unit. The feed stream will then preferably contain an admixture of all of the $C_3$-minus hydrocarbons and may also contain small amounts of such gases as water vapor, nitrogen, water vapor and carbon dioxide. In addition, a gas stream derived from an FCC unit may be expected to contain hydrogen unless removed by prior processing. The feed gas stream may also contain some $C_4$ hydrocarbons including the butylenes. However, the concentration of $C_4$ hydrocarbons in the feed stream is preferably below about 10 mole percent. It is expected that the feed stream will be produced in a gas concentration unit in which there is no attempt made to recover $C_3$ hydrocarbons as a separate product stream. The olefin-containing feed stream preferably comprises at least 10 mole percent olefins and more preferably at least 30 mole percent olefins.

The feed stream is charged to a hydration zone. In the subject invention, it is preferred to use a direct hydration process due to the economical operation of this process as compared with the indirect hydration processes presently available. There are several direct hydration processes in commercial operation. One of these processes is a gas phase hydration, which employs a fixed bed catalyst comprising a supported phosphoric acid. This process is described at page 195 of the November 1967 issue of *Hydrocarbon Processing*. A second type of direct hydration process is the liquid phase hydration which occurs in the presence of a dissolved tungsten containing catalyst. Two variations of this process are described in the previously cited U.S. Pat. Nos. 3,758,615 and 3,450,777. A direct hydration process using a pelleted tungsten-containing catalyst is described in U.S. Pat. No. 3,452,106. This catalyst is described as being effective for the hydration of both ethylene and propylene at similar conditions.

A third type of direct hydration process is a mixed phase process in which both gas and liquid phase hydrocarbons are present and a cation exchange resin-type catalyst is employed. This process was also described in the previously cited references. It is peferred that such a resin-type catalyst is employed in the subject process. For this reason, the bulk of the description herein will be in terms of the use of this type of catalyst. However, it is not intended to thereby limit the scope of the subject invention to the use of a resin-type catalyst since other catalysts, including those not yet developed, may prove superior in this application. In this regard, it is specifically recognized that the presently available resin-type catalysts are limited in the maximum temperatures at which they may be employed. This is of direct significance to the subject process in that the temperature desired for the hydration of ethylene is higher than the temperature normally employed for the direct hydration of propylene. The temperatures now necessary to obtain high ethylene hydration rates are in fact above the desired operating temperatures for these resin-type catalysts. More specifically, it is presently preferred that a resin-type catalyst is not operated at a temperature above about 180° C. On the other hand, a temperature on the order of about 200° C. is necessary to maintain a 30-40% conversion of ethylene to ethanol by known present technology. For this reason, in the subject process, there is no attempt to maximize the direct hydration of ethylene when the preferred resin-type is utilized since to do so will result in premature deactivation of the catalyst. This limited conversion is acceptable in the subject process, although a high conversion would be highly desired, since the objective of the process is not the conversion of the entire olefinic content of the feed stream to alcohols. Rather, the objective is the upgrading of the entire feed stream to more salable products. In this regard, it should be pointed out that some of the previously cited references, specifically those directed to the tungsten-containing catalysts, indicate that overlapping temperature ranges exceeding 200° C., are preferred for the hydration of both ethylene and propylene.

The olefin feed stream is admixed with water and passed into the hydration reaction zone. Preferably, the hydration reaction zone is located in the upper portion of a hydration zone which comprises a single vertical tower-like vessel having suspended therein one or more beds of the solid hydration catalyst. Preferably, the reaction zone is operated as a trickle bed-type reactor, with the olefin-water feed admixture entering the top of the reactor and passing downward through the catalyst to a void volume located in the lower portion of the vessel. This void volume is preferably employed as an initial vapor-liquid separation zone which receives the actual reaction zone effluent. Vapors comprising hydrogen, the inert paraffins and residual olefinic hydrocarbons may be withdrawn on a pressure control basis from this void volume. An aqueous phase collects in the bottom of the void volume and may be withdrawn on level control. The hydration reaction is exothermic, and it is therefore preferred that additional amounts of relatively low temperature water are injected into the descending reactants at several points along the height of the catalyst-containing zone within the reaction vessel. This mode of operation is described in greater detail in the previously cited references.

The olefin-water feed admixture to the reaction vessel should contain at least a molar excess of water over that which is stoichiometrically required for the hydration reaction. The water concentration within the reaction zone is an important variable in the process. It is preferred that the molar ratio of water to entering olefinic hydrocarbon is between about 5:1 and 20:1. More preferably, this ratio is between about 8:1 and about 20:1. Each mole of the olefinic hydrocarbon charged to the reaction vessel therefore requires the addition of from about 8 to about 20 moles of water. Since only a small proportion of this water is consumed in the hydration reaction, the product alcohol is withdrawn from the hydration reaction vessel as a part of a relatively dilute aqueous alcohol solution. This dilution increases the cost of the various distillation methods of product recovery.

The hydration conditions which are suitable for the subject process include a pressure of from about 30 to about 200 atmospheres. Preferably, the hydration reactor is maintained at a pressure of from about 40 to about 125 atmospheres absolute. The hydration reaction zone is preferably operated at a temperature between about 120° and about 180° C. when resin-type catalysts are employed. An operating inlet temperature between about 135° and about 160° C. is useful to promote propylene conversion and extend catalyst life. These conditions are those which are preferred for the conversion of propylene to isopropyl alcohol. In this instance, it has been characterized as maintaining the propylene as a supercritical gas and the water as a liquid. Other conditions and operating methods may be preferred with catalysts other than the preferred resin-type catalyst. For instance, in the preferred hydration system shown in the Drawing, the great majority of the alcohols are withdrawn in a liquid phase stream which is rich in water. A vapor phase stream is also removed from the hydration zone for the purposes of pressure control. Most hydration systems do not have such a separate vapor withdrawal, and the hydration zone effluent is then the total reaction zone effluent. The rate of water flow through the catalyst bed is preferably between about 1 and about 40 and preferably about 5 and about 25 moles of water per $cm^2$ of cross sectional area per hour. The liquid hourly space velocity of the entering olefinic hydrocarbon should be between about 0.05 and about 2, and is preferably between about 0.1 and 1.0.

The subject process may be employed utilizing the presently preferred catalyst or those which are the result of the continuing research effort in this area. It is preferred that a solid particulate catalyst is employed. The presently preferred hydration catalysts are ion exchange catalysts or resins. The preferred resins comprise a copolymer of styrene and divinylbenzene. It is further preferred that these copolymer resins are treated with a sulfur-containing acid to yield a highly acidic sulfonic acid-containing resin. In general, the catalyst should contain from about 0.2 to 1 sulfonic acid group per aromatic ring present in the resin. These catalysts may be further modified as by chlorination, fluorination, etc., which has been shown to yield improved high temperature stability. A particularly preferred resin of this nature is described in the previously referred to U.S. Pat. No. 4,340,769, incorporated herein by reference. Suitable catalysts are available from commercial sources.

The liquid phase aqueous stream withdrawn from the hydration zone will contain an admixture of the product alcohols, water, paraffinic hydrocarbons, unreacted olefinic hydrocarbons, and the various possible reaction by-products such as ethers and ketones. It is preferred that this admixture is subjected to one or more flash operations which generate a vapor phase comprising the more volatile components present in the effluent. This vapor phase will be an admixture of hydrocarbons present in the effluent stream. These vapors are preferably passed directly into the hydrogenation zone in admixture with any vapor stream removed from the reaction vessel as described above. The product alcohols remain in the aqueous liquid phase portion withdrawn from the separation step. Depending on the conditions desired for use within the hydration reaction zone in the downstream hydrogenation and fractionation zones, these flashing steps may be limited or eliminated. However, the use of one such flash separation is presently preferred.

The remaining liquid phase portion of the aqueous stream removed from the hydration reaction vessel is preferably passed into a fractionation zone for the recovery of the dissolved alcohols. Other types of product recovery methods including solvent extraction or semipermeable membrane technology can also be employed. For instance, it has been suggested in the art to extract alcohol using gasoline boiling range hydrocarbons as the solvent. Preferably, the fractionation zone comprises at least one trayed fractionation column to perform an initial rough separation. Azeotropic mixtures normally require two or more columns to achieve a high degree of water rejection. Alcohol fractionation systems used to remove water often employ extractive distillation techniques. Other types of fractionation equipment such as packed columns and the recently developed distillation devices which employ rotating internal elements may also be employed. An alcohol-containing material may be removed from the fractionation zone as the net product stream. Alternatively, this material may be processed in additional fractionation, extractive distillation or by liquid-liquid extraction to increase the purity of the alcohol products. The remainder of the compounds entering the fractionation zone are concentrated into a net effluent stream which is basically water with a small amount of residual alcohols and other compounds. The effluent stream is preferably recycled within the process, although it may be necessary to remove certain impurities such as sodium or metal ions. This is basically to prevent detrimental effects to the hydration catalyst. If necessary, such water treatment may be performed using cation and anion exchangers. Additional information on the separation of alcohols may be obtained from standard references and other sources such as U.S. Pat. Nos. 3,445,345; 3,955,939; 3,990,952; 4,161,429; and 4,382,843.

The olefin-containing process stream which is separated from the hydrocarbons which have passed through the hydration zone is passed into a hydrogenation zone. The function of this zone is the conversion of remaining olefinic hydrocarbons to their corresponding saturated hydrocarbons. This is a very mild (easy to perform) hydrogenation operation. The hydrogenation may therefore be performed using readily available commercial catalyst at only slightly elevated temperatures and pressures. For instance, it is believed the olefins may be saturated at a temperature of approximately 100° C. or higher in the presence of hydrogen equal to about 110 to about 130 mole percent of the stoichiometrically required amount of hydrogen. The hydrogen present in the feed gas stream may be sufficient. Additional hydrogen may be passed into the hydrogenation reactor, but this is not preferred as it is desired to maximize the utilization of the feed gas hydrogen. The hydrogenation reactor may be maintained at a pressure in the range of from about 100 to about 1200 psig although lower pressures on the order of about 600 psig are preferred. It may be noted that many of the hydration processes operate at relatively high pressure, and the hydrogenation reactor may be operated at the same pressure as the hydration reactor except for the inherent pressure drops associated with the process conduits, vessels and flow control apparatus located between these two reaction zones. However, with the preferred flashing of liquids removed from the hydration reactor, it is preferred that the hydrogenation reactor is operated at a lower pressure than the hydration reactor. It is preferred that the olefin-containing process stream is passed downward through a fixed bed of the hydrogenation catalyst as a vapor phase stream.

The preferred hydrogenation catalysts comprise from about 0.1 to about 0.5 wt.% platinum and a similar amount of lithium deposited on spherical alumina particles. The catalyst may also be in the form of an extrudate or pill. It is preferred that the active components of the catalysts are deposited onto the alumina support after the formation of the support rather than by admixture into the support means prior to the dropping or extrusion of the solid support. The solid support particle can therefore be soaked, dipped or otherwise immersed in a solution comprising a suitable compound of the active components. The catalyst is then preferably dried and then reduced in a flowing gas at a temperature in excess of 700° F. in the presence of hydrogen. Instead of the preferred platinum, other metals including cobalt, nickel, and palladium or a mixture of these metals may be employed as the active catalytic agent. Another preferable catalyst is nickel supported on kieselguhr.

The effluent stream of the hydrogenation zone is preferably passed through an indirect heat exchanger in which it is cooled sufficiently to effect a partial condensation of the hydrocarbons present in this stream. Such light gases as hyrogen, nitrogen, methane, and carbon dioxide are not condensed at this point. Essentially all of the propane is preferably condensed. The uncondensed gases including ethane may be removed from the process for use as a fuel gas. A portion of this gas may be recycled to the hydrogenation zone if it has a significant hydrogen concentration. The condensed propane is removed as an LPG stream having a low olefin content. Such low olefin contents are desirable in an LPG stream as evidenced by the fact that the olefin content is one of the quality indicators of LPG. The product LPG may be combined with other streams, such as those containing butanes, or may be sold or used as produced.

In accordance with this description, a preferred embodiment of the invention may be characterized as a hydrocarbon conversion process which comprises the steps of passing a feed stream comprising an admixture of $C_3$-minus hydrocarbons removed from a gas concentration unit of a fluidized catalytic cracking process into a hydration zone operated at hydration-promoting conditions and in which ethylene and propylene are converted to the corresponding monohydric alcohols in the presence of a solid hydration catalyst and a molar excess of water and producing a hydration zone effluent stream which comprises hydrogen, methane, ethane, propane, ethylene, propylene, ethanol, propanol, and water; separating the hydration zone effluent stream into a vapor phase process stream which comprises hydrogen, methane, ethane, propane, ethylene, and propylene and which contains less than 10 mole percent alcohols and a liquid phase process stream which comprises water, ethanol, and propanol; recovering ethanol and propanol from the liquid phase process stream; passing the vapor phase process stream through a hydrogenation zone wherein the vapor phase process stream is contacted with a solid catalyst at olefin hydrogenation conditions and thereby producing a hydrogenation zone effluent stream comprising ethane and propane; and recovering an LPG product stream from the hydration zone effluent stream.

I claim as my invention:

1. A process for the production of lower alcohols which comprises the steps of:
   (a) passing a feed gas stream which comprises methane, ethane, ethylene, propane, and propylene into a hydration zone operated at conditions effective to convert a portion of the entering olefins to alcohols and thereby producing a hydration zone effluent stream which comprises methane, ethane, ethylene, propane, propylene, ethanol, and propanol;
   (b) separating an alcohol product stream comprising ethanol and propanol from the hydration zone effluent stream and thereby forming a process stream which comprises methane, ethane, ethylene, propane, and propylene;
   (c) passing the process stream through a hydrogenation zone operated at conditions effective to saturate ethylene and propylene and producing a hydrogenation zone effluent stream; and,
   (d) recovering an LPG product stream comprising propane from the hydrogenation zone effluent stream.

2. The process of claim 1 further characterized in that the feed stream contains less than 10 mole percent $C_4$-plus hydrocarbons.

3. The process of claim 2 further characterized in that the feed stream is derived from the hydrocarbon effluent stream of a fluidized catalytic cracking process.

4. The process of claim 3 further characterized in that a resin-type catalyst is employed in the hydration zone.

5. The process of claim 4 further characterized in that a hydration catalyst comprising a sulfonated styrene-divinylbenzene copolymer resin is present in the hydration zone.

6. The process of claim 3 further characterized in that a hydration catalyst comprising a heteropoly acid of tungsten is employed in the hydration zone.

7. The process of claim 3 further characterized in that the feed gas stream and the process stream comprise hydrogen.

8. A hydrocarbon conversion process which comprises the steps of:
   (a) passing a feed stream comprising an admixture of $C_3$-minus hydrocarbons removed from a gas concentration unit of a fluidized catalytic cracking process into a hydration zone operated at hydration-promoting conditions and in which ethylene and propylene are converted to the corresponding monohydric alcohols in the presence of a solid hydration catalyst and a molar excess of water and producing a hydration zone effluent stream which comprises hydrogen, methane, ethane, propane, ethylene, propylene, ethanol, propanol, and water;
   (b) separating the hydration zone effluent stream into a vapor phase process stream which comprises hydrogen, methane, ethane, propane, ethylene, and propylene and which contains less than 10 mole percent alcohols and a liquid phase process stream which comprises water, ethanol, and propanol;
   (c) recovering ethanol and propanol from the liquid phase process stream;
   (d) passing the vapor phase process stream through a hydrogenation zone wherein the vapor phase process stream is contacted with a solid hydrogenation catalyst at olefin hydrogenation conditions and thereby producing a hydrogenation zone effluent stream comprising ethane and propane; and,
   (e) recovering an LPG product stream from the hydration zone effluent stream.

9. The process of claim 8 further characterized in that the feed stream and the hydrogenation zone effluent stream comprise methane.

10. The process of claim 8 further characterized in that the hydration catalyst is a resin-type catalyst.

11. The process of claim 8 further characterized in that the hydration zone effluent stream is a vapor phase stream, which is partially condensed to yield the liquid phase process stream.

12. The process of claim 8 further characterized in that the hydration catalyst comprises tungsten.

13. The process of claim 12 further characterized in that the hydration catalyst comprises a heteropoly acid of tungsten.

* * * * *